US008664583B2

(12) United States Patent
Hunt et al.

(10) Patent No.: US 8,664,583 B2
(45) Date of Patent: Mar. 4, 2014

(54) NONLINEAR OPTICAL SURFACE SENSING WITH A SINGLE THERMO-ELECTRIC DETECTOR

(75) Inventors: Jeffrey H. Hunt, Thousand Oaks, CA (US); John H. Belk, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 206 days.

(21) Appl. No.: 13/175,563

(22) Filed: Jul. 1, 2011

(65) Prior Publication Data
US 2013/0001407 A1 Jan. 3, 2013

(51) Int. Cl.
*G02F 1/01* (2006.01)

(52) U.S. Cl.
USPC ........ 250/225; 250/316.1; 977/953; 977/954; 977/955

(58) Field of Classification Search
USPC ...................................... 250/316.1
See application file for complete search history.

(56) References Cited

U.S. PATENT DOCUMENTS

| | | | |
|---|---|---|---|
| 6,788,405 B2 | 9/2004 | Hunt | |
| 6,891,660 B2 | 5/2005 | Hunt et al. | |
| 6,924,925 B2 | 8/2005 | Hunt et al. | |
| 6,996,147 B2 * | 2/2006 | Majumdar et al. | 372/43.01 |
| 2003/0234360 A1 | 12/2003 | Hunt | |
| 2008/0170982 A1 * | 7/2008 | Zhang et al. | 423/447.3 |
| 2008/0251723 A1 * | 10/2008 | Ward et al. | 250/338.4 |
| 2008/0310790 A1 * | 12/2008 | Wu et al. | 385/12 |
| 2009/0072145 A1 * | 3/2009 | Peczalski et al. | 250/339.04 |
| 2009/0108202 A1 * | 4/2009 | Gritz et al. | 250/338.1 |

FOREIGN PATENT DOCUMENTS

| | | |
|---|---|---|
| WO | 2010478844 A2 | 4/2010 |
| WO | 2010135439 A2 | 11/2010 |

OTHER PUBLICATIONS

Combined Search and Examination Report for Patent Application No. GB1211835.2, Sep. 28, 2012 (pp. 4-6).
C.A. Huber et al., Nanowire Array Composites, Science 263, pp. 800-802 (1994).
T.E. Huber et al., Confinement Effects and Surface Charge in Bi Nanowires, Appl. Phys. Lett. 84, pp. 1326-1328 (2004).
P. Jones et al., Electrical contact resistance of individual bismuth telluride nanowires, Proc. 25th Int. Conf. Thermoelectrics held 2006 (IEEE, Piscattaway, 2007). pp. 693-696.
Optoelectronics and Nanophotonics NASA article [See http://www.nasa.gov/centers/ames/research/technology-onepagers/optoelectronics.html], Retrieval date: Feb. 10, 2011.

* cited by examiner

*Primary Examiner* — David Porta
*Assistant Examiner* — Djura Malevic
(74) *Attorney, Agent, or Firm* — Vista IP Law Group LLP; Cynthia A. Dixon (57) ABSTRACT

An apparatus, system, and method are disclosed for nonlinear optical surface sensing with a single thermo-electric detector. In particular, the system includes at least two signal sources that are co-aligned to propagate photons to the same location on a surface. The system also includes at least one focusing element that focuses a sequence of photons that is reflected from the location on the surface. In addition, the system includes at least one frequency selective electromagnetic detector that detects the sequence of photons that are focused from the focusing element(s). When the frequency selective electromagnetic detector senses a photon, the frequency selective electromagnetic detector emits an electrical pulse that has a voltage that is proportional to the energy level of the photon. Additionally, the system includes a processor that processes the electrical pulses, and de-multiplexes the sequence of emitted electrical pulses based on the electrical pulse voltage of the electrical pulses.

22 Claims, 4 Drawing Sheets

NONLINEAR OPTICAL SURFACE SENSING WITH A SINGLE THERMO-ELECTRIC DETECTOR

BACKGROUND

The present disclosure relates to nonlinear optical surface sensing. In particular, it relates to nonlinear optical surface sensing with a single thermo-electric detector.

SUMMARY

The present disclosure relates to an apparatus, system, and method for nonlinear surface sensing with a single thermo-electric detector. In one or more embodiments, the disclosed system for nonlinear electromagnetic surface sensing includes at least two signal sources that are co-aligned to propagate photons to the same location on a surface to be reflected off of the surface. The system further includes at least one focusing element that focuses a sequence of photons that is reflected from the same location on the surface. Also, the system includes at least one frequency selective electromagnetic detector that detects the sequence of photons that are focused from the focusing element(s). When the frequency selective electromagnetic detector(s) senses at least one photon, the frequency selective electromagnetic detector(s) emits an electrical pulse(s) that has a voltage that is proportional to the energy level of the sensed photon(s). In addition, the system includes at least one processor that processes at least one electrical pulse, and de-multiplexes the sequence of electrical pulses based on the voltage of the electrical pulses.

In one or more embodiments, the disclosed system for nonlinear electromagnetic surface sensing is used for nonlinear optical surface sensing. In at least one embodiment, the system further includes at least one intensity control device that selects a range of the rate of arrival of the photons. In some embodiments, at least one intensity control device is an electromagnetic energy filtering device. In one or more embodiments, the system further includes at least one polarization control device that selects the polarization of the photons. In at least one embodiment, at least one polarization control device is a polarizer. In some embodiments, the polarizer selects at horizontal polarization, vertical polarization, left-hand polarization, and/or right-hand polarization. In one or more embodiments, at least one focusing element is a signal collection lens.

In one or more embodiments, at least one frequency selective electromagnetic detector includes a nanowire array constructed from a plurality of nanowires of different compositions. A nanowire has a diameter in a size range associated with nanoparticles, which are 1-100 nanometers (nm) in size. The length of a nanowire is longer than the diameter of the nanowire, and the length of a nanowire can be in a size range from millimeters (mm) to centimeters (cm). In the nanowire array, at least one nanoparticle-sized diameter thermoelectric junction is formed between the nanowires of different compositions. During operation of the detector, when at least one nanoparticle-sized diameter thermoelectric junction senses at least one photon, the nanoparticle-sized diameter thermoelectric junction(s) emits at least one electrical pulse voltage that is proportional to the energy level of the photon(s) that is sensed.

In one or more embodiments, at least one of the nanowires in the nanowire array is manufactured from a compound material including Bismuth (Bi) and Tellurium (Te). In at least one embodiment, the detector is a frequency selective optical detector that is used to sense photons having optical frequencies. In some embodiments, the material of at least one of the nanowires is selected according to the frequency of the photons that are desired to be sensed. In one or more embodiments, the diameter of at least one nanoparticle-sized diameter thermoelectric junction is selected according to the frequency of the photons that are desired to be sensed.

In one or more embodiments, the method for nonlinear electromagnetic surface involves propagating, by at least two signal sources that are co-aligned, photons to the same location on a surface. The method further involves reflecting the photons off of the surface to produce a sequence of photons. In addition, the method involves focusing, by at least one focusing element, the sequence of photons that is reflected from the surface. The method also involves detecting, by at least one frequency selecting electromagnetic detector, the sequence of photons that were focused by the focusing element(s). Additionally, the method involves emitting, from the frequency selective electromagnetic detector(s), a sequence of electrical pulses, where each of the electrical pulses has a voltage that is proportional to the energy level of its respective detected photon. Also, the method involves processing, with at least one processor, the sequence of electrical pulses. Further, the method involves de-multiplexing, with at least one processor, the sequence of electrical pulses based on the voltage of the electrical pulses.

In at least one embodiment, the method is used for nonlinear optical surface sensing. In one or more embodiments, the method further comprises selecting, with at least one intensity control device, a range of a rate of arrival of the photons. In some embodiments, the method further comprises selecting, with at least one polarization control device, a polarization of the photons.

The features, functions, and advantages can be achieved independently in various embodiments of the present disclosure or may be combined in yet other embodiments.

DRAWINGS

These and other features, aspects, and advantages of the present disclosure will become better understood with regard to the following description, appended claims, and accompanying drawings where:

DESCRIPTION

The methods and apparatus disclosed herein provide an operative system for nonlinear optical surface sensing with a single thermo-electric detector. In particular, the present disclosure uses nanowires to build a frequency selective electromagnetic detector to be employed by the disclosed system for nonlinear optical surface sensing. For the frequency selective electromagnetic detector, the nanowires are constructed in a nanowire array. The nanowire array allows for the detector to be able to convert the detected electromagnetic signals into electrical signals, while maintaining the wavelength (i.e. frequency) information associated with the detected electromagnetic signals.

The disclosed frequency selective electromagnetic detector is preferably a frequency selective optical detector for sensing photons having optical frequencies. However, in alternative embodiments, the disclosed frequency selective electromagnetic detector may be manufactured to detect frequencies of electromagnetic radiation other than optical frequencies. In addition, the nanowires are preferably manufactured from a compound material containing Bismuth (Bi) and Tellurium (Te) (e.g., Bismuth Telluride ($Bi_2Te_3$)). However, in other embodiments of the present disclosure, the nanowires may be manufactured from other materials that exhibit thermoelectric properties that are similar to the thermoelectric properties of Bismuth Telluride.

In order to better understand the features of the disclosed frequency selective electromagnetic detector, a brief discussion regarding conventional optical sensors is presented. Conventional optical sensors typically operate as bulk frequency absorption devices. In fact, most conventional optical detectors employ bulk semiconductors (e.g., avalanche photodiodes (APD)), which absorb electromagnetic radiation across large frequency ranges and have no means to discriminate against electromagnetic radiation in specific frequency ranges. In order to achieve increased bandwidth, these optical systems operate using multiple narrow frequency bands, which have wavelengths that are approximately 1.5 microns in length. These optical systems present a technical challenge because they require a mechanism to separate out the many optical frequencies that are operational.

In order to make the conventional optical sensors be wavelength selective, optical elements (e.g., filters, diffraction gratings, etc.) must be placed in the optical path in front of the optical sensor to only allow the electromagnetic radiation of interest to reach the sensor. The inclusion of these optical elements introduces a disadvantage to these optical systems because they add additional size, weight, and complexity to the optical systems. In addition, it should be noted that some conventional optical sensors require their optical elements to be in strict alignment with the optical path in order to make them operational. As such, considerable effort is required to simply make these optical systems operational.

Optical signal detection that can detect both low light levels while maintaining wavelength sensitivity is very challenging to achieve. Currently, most optical signal detection is performed using avalanche photodiodes. An avalanche photodiode is a device that has a gain on the order of several orders of magnitude. An avalanche photodiode detector collects a small amount of light, and converts it to a proportional electrical signal. A separate processing system is then needed to reassemble the signal.

The system of the present disclosure uses nanoparticle-sized diameter thermoelectric junctions to be able to achieve quantum sensing that is wavelength sensitive. When a thermoelectric element is exposed to light, the electromagnetic field is dissipated in the element, and the energy that is deposited generates electrical power that can be used for sensing the light. This type of thermoelectric element is generally referred to as a bolometer. Generally, a bolometer is a device for measuring the energy of incident electromagnetic radiation.

It is possible to fabricate nanoparticle-sized bolometers from nanoparticle-sized diameter junctions between nanowires of different compositions. These nanoparticle-sized diameter junctions respond to individual photons by emitting an individual electrical pulse having a voltage that is proportional to the temperature change caused by the absorption of the photon. The temperature change is proportional to the energy of the photon. Thus, these nanoparticle-sized diameter junctions are sensitive to wavelength. It should be noted that recently, it has been demonstrated that as the wire diameter of a nanowire is reduced, thermal transport in the nanowire is drastically decreased because of less phonon scattering within the nanowire walls.

Currently, the detectors that operate in the single photon regime are limited to photomultipliers and avalanche photodiodes. Neither of these types of devices has wavelength selectivity. Photomultipliers are constructed from tubes that are very delicate and, thus, they can easily be damaged. Avalanche photodiodes must operate in Geiger mode for them to achieve single photon detection. As such, avalanche photodiodes are extremely noisy, and have long dead times after they detect a photon. The frequency selective electromagnetic detector of the present disclosure will not only solve the problems associated with each of these two types of detectors, but will also allow for wavelength selectivity.

It should be noted that since the disclosed system for nonlinear optical surface sensing is wavelength sensitive, the disclosed system does not have the requirement for frequency separation prior to detection. The disclosed system is able to detect all of the signals on a single detector, and sort out the signal frequencies after the detection has been performed. In other words, instead of separating out the optical signal carrier frequencies before the signals enter the detector, the signal sorting can be accomplished after detection, when the electronic signals can be more rapidly processed. This feature allows for a significant reduction in both the complexity of the system hardware and the number of detectors required for the processing.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
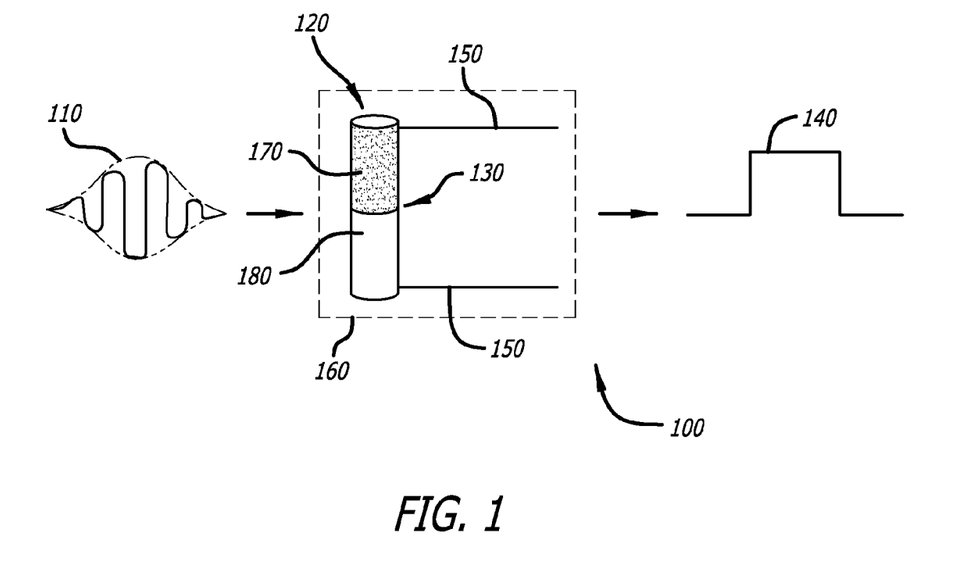
FIG. 1 illustrates a simplified block diagram of the disclosed frequency selective electromagnetic detector during operation, in accordance with at least one embodiment of the present disclosure.

FIG. 1 shows a simplified block diagram of the disclosed frequency selective electromagnetic detector 160 during operation 100, in accordance with at least one embodiment of the present disclosure. In this figure, a photon 110 is shown to be propagated towards the frequency selective electromagnetic detector 160. The photon 110 has a frequency (v), which is proportional to its level of energy (E). Energy (E) is equal to hv, where h is equal to the Planck constant. It should be noted that for a given frequency (v), its corresponding wavelength (λ) is equal to c/v, where c is equal to the speed of light.

Also in this figure, the frequency selective electromagnetic detector 160 is shown to include a composite nanowire 120, which is fabricated from two different materials 170, 180. Two electrical terminals 150 are shown to be connected to each end of the nanowire 120. The nanowire 120 has a nanoparticle-sized diameter thermoelectric junction 130 that is formed between the two different materials 170, 180. During operation of the disclosed frequency selective electromagnetic detector 160, when the nanoparticle-sized diameter thermoelectric junction 130 senses a photon 110, the nanoparticle-sized diameter thermoelectric junction 130 emits an electrical pulse 140 via the electrical terminals 150. The voltage of the emitted electrical pulse 140 is proportional to the photon's 110 level of energy and, thus, the magnitude of the emitted electrical pulse 140 can be used to determine the photon's 110 associated frequency.

With regard to the nanoparticle-sized diameter thermoelectric junction 130, the thermoelectric effect is the effect in the nanoparticle-sized diameter thermoelectric junction 130 where a temperature difference causes a voltage to be generated. Typically, values are measured in microvolts (µV) per Kelvin (K). When a temperature difference is applied to the nanoparticle-sized diameter thermoelectric junction 130, the charge carriers in the nanowire 120, whether they are electrons or holes, diffuse from the nanoparticle-sized diameter thermoelectric junction 130 to the connecting electrical terminals 150. In this way, the behavior is similar to the way that a classical gas expands when heated. As a result, the mobile charge carriers migrating to the electrical terminals 150 leave behind their oppositely charged and immobile nuclei at the nanoparticle-sized diameter thermoelectric junction 130, thus giving rise to a thermoelectric voltage. As such, the nanoparticle-sized diameter thermoelectric junction 130 is in essence operating as a thermoelectric semiconductor.

As previously mentioned, the frequency selective electromagnetic detector 160 is preferably manufactured from a compound material containing Bismuth (Bi) and Tellurium (Te), such as Bismuth Telluride ($Bi_2Te_3$). However, the frequency selective electromagnetic detector 160 may be manufactured from other materials that exhibit thermoelectric properties that are similar to the thermoelectric properties of Bismuth Telluride. In general, the materials to be used are selected according to the desired operational frequency range of the frequency selective electromagnetic detector 160. In addition, it should be noted that the diameter of the nanoparticle-sized diameter thermoelectric junction 130 will also generally be selected according to the desired operational frequency range. Also, it should be noted that the disclosed frequency selective electromagnetic detector 160 may be manufactured to include one or more nanowires 120.

The operational frequency detection regime of any material operating as a conventional semiconductor is limited to shorter wavelengths because photons having longer wavelengths do not have enough energy to excite the electrons across the material band gap. When wavelengths have photon energy that is below that of the material band gap, the semiconductor material will not respond. Operating as a thermoelectric semiconductor, Bismuth Telluride (BiTe) has a very small band gap. Depending upon the exact composition of the BiTe material, the band gap will be approximately 30-50 milli electron volts (meV). Thus, the implication is that the disclosed frequency selective electromagnetic detector 160, when manufactured from BiTe, will operate as a frequency selective optical detector from the soft ultraviolet (UV) spectrum (~300 nanometers (nm)) throughout the visible light spectrum (~400 to 770 nm) well into the infrared spectrum (~770 nm to 20 microns).

It should be noted that in alternative embodiments, the frequency selective electromagnetic detector 160 includes a nanowire 170, which is fabricated from a single material 170. The nanowire 170 is connected to an electrical conductor 180 (e.g., an electrode 180), which is connected to an electrical terminal 150. The opposite end of the nanowire 170 that is connected to the electrical conductor 180 is connected to a different electrical terminal 150. A nanopartical-sized diameter thermoelectric junction 130 is formed between the nanowire 170 and the electrical conductor 180. During operation of the disclosed frequency selective electromagnetic detector 160, when the nanoparticle-sized diameter thermoelectric junction 130 senses a photon 110, the nanoparticle-sized diameter thermoelectric junction 130 emits an electrical pulse 140 via the electrical terminals 150. The voltage of the emitted electrical pulse 140 is proportional to the photon's 110 level of energy and, thus, the magnitude of the emitted electrical pulse 140 can be used to determine the photon's 110 associated frequency.

With regard to the nanoparticle-sized diameter thermoelectric junction 130, the thermoelectric effect is the effect in the nanoparticle-sized diameter thermoelectric junction 130 where a temperature difference causes a voltage to be generated. Typically, values are measured in microvolts (µV) per Kelvin (K). When a temperature difference is applied to the nanoparticle-sized diameter thermoelectric junction 130, the charge carriers in the nanowire 170, whether they are electrons or holes, diffuse from the nanoparticle-sized diameter thermoelectric junction 130 to the connecting electrical terminals 150. In this way, the behavior is similar to the way that a classical gas expands when heated. As a result, the mobile charge carriers migrating to the electrical terminals 150 leave behind their oppositely charged and immobile nuclei at the nanoparticle-sized diameter thermoelectric junction 130, thus giving rise to a thermoelectric voltage. As such, the nanoparticle-sized diameter thermoelectric junction 130 is in essence operating as a thermoelectric semiconductor.

For these embodiments, the nanowire 170 is manufactured from Bismuth (Bi) and, the electrical conductor 180 is manufactured from Copper (Cu). However, the nanowire 170 may be manufactured from various other materials that exhibit thermoelectric properties that are similar to the thermoelectric properties of Bismuth Telluride or Bismuth nanowires. In addition, the electrical conductor 180 may be manufactured from various other conductor materials other than Copper. In general, the materials to be used are selected according to the desired operational frequency range of the frequency selective electromagnetic detector 160. In addition, it should be noted that the diameter of the nanoparticle-sized diameter thermoelectric junction 130 will also generally be selected according to the desired operational frequency range. In addition, it should be noted that the disclosed frequency selective electromagnetic detector 160 may be manufactured to include one or more nanowires 170.

Figure 2:
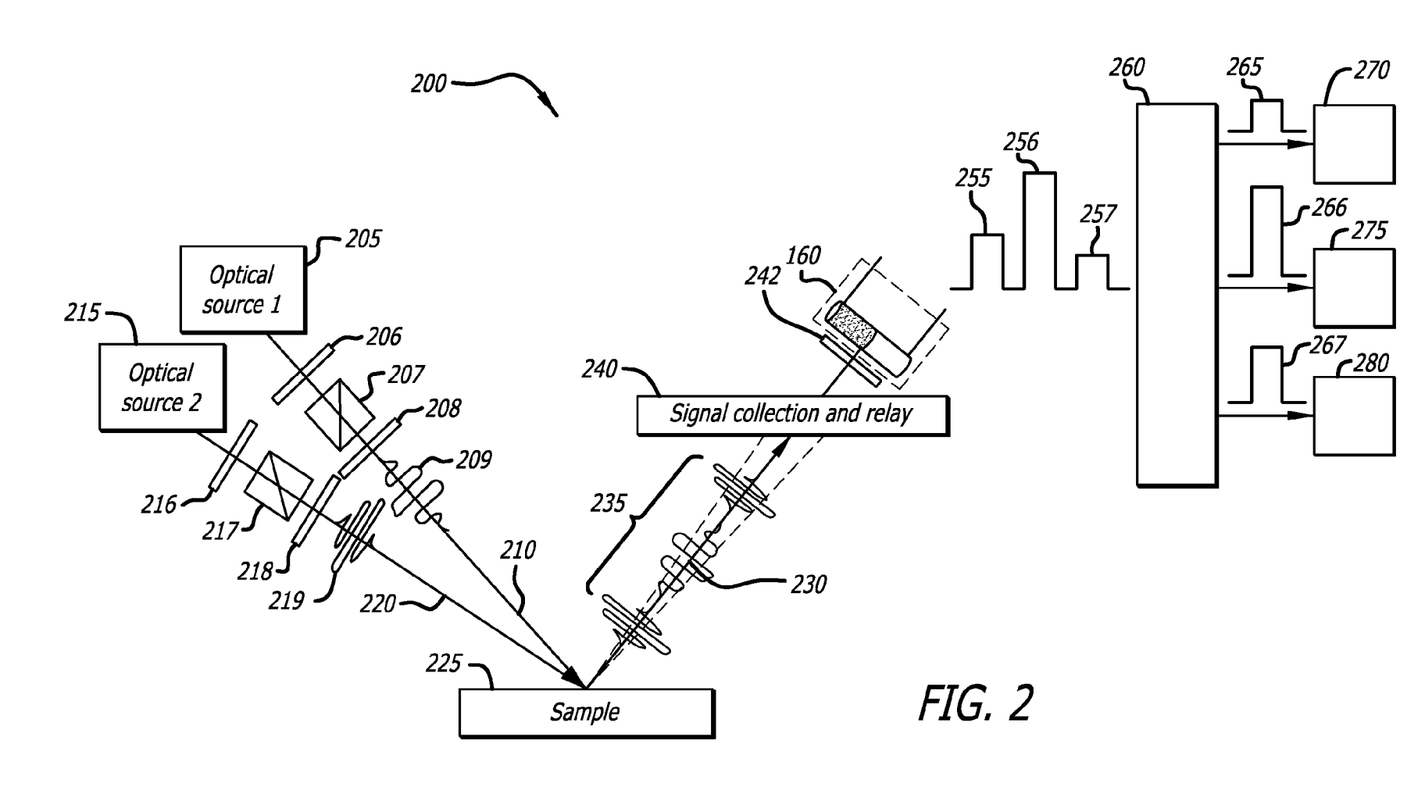
FIG. 2 shows a simplified block diagram of the disclosed system for nonlinear optical surface sensing with a single thermo-electric detector, which employs the frequency selective electromagnetic detector of FIG. 1, in accordance with at least one embodiment of the present disclosure.

FIG. 2 shows a simplified block diagram of the disclosed system 200 for nonlinear optical surface sensing with a single thermo-electric detector, which employs the frequency selective electromagnetic detector 160 of FIG. 1, in accordance with at least one embodiment of the present disclosure. In order to understand the operation of the disclosed system 200, the path of a couple of photons 209, 219 travelling through the system 200 is described. It should be noted that each of the photons 209, 219 has a different wavelength (i.e. the photons are multi-spectral). As such, each photon 209, 219 also has a different frequency, f1 and f2, respectively.

In this figure, the photons 209, 219 are each emitted from a different signal source 205, 215. The two signal sources 205, 215 are co-aligned such that they will both propagate photons to the same location of a sample 225 to be interrogated. The photons 209, 219 are then each propagated into an intensity control device 206, 216. The intensity control devices 206, 216 are used to set a range of operation for the disclosed system 200 (i.e. to select a range of the rate of arrival of the photons that are desired to be sensed) and, thus, they operate as electromagnetic filtering devices. Types of devices that may be employed for the disclosed intensity control devices 206, 216 include, but are not limited to, a neutral-density filter and a dark color filter.

The photons 209, 219 are then outputted from the intensity control devices 206, 216, and are propagated into polarization control devices 207, 217. The polarization control devices 207, 217 are utilized for selecting a polarization of the photons that are desired to be sensed and, as such, they operate as a polarizer. In one or more embodiments, the polarization control devices 207, 217 may select various different polarizations including, but not limited to, horizontal polarization, vertical polarization, left-hand circular polarization, and right-hand circular polarization. Types of devices that may be used for the disclosed polarization control devices 207, 217 include, but are not limited to, a polarization plate, a Brewster's angle polarizer, and a thin film polarizer. The precise type of polarizer device to be selected for the system 200 depends upon the particular engineering requirements, such as the polarization rejection ratio, the size and weight limitations of the polarizer, and the wavelength range of operation.

From the output of the polarization control devices 207, 217, the photons 209, 219 are propagated to the same location on a sample surface 225. The photons 209, 219, which are shown to be in beams 210 and 220, respectively, illuminate the sample 225, which causes the sample 225 to emit a beam 230 that contains a sequence of photons 235 having multiple frequencies (f1, f2, f1+f2, f1−f2, 2/1, 2/2). The frequencies of the sequence of photons 235 can be used to characterize the sample 225.

The beam 230 emitted from the sample 225 is then propagated onto the collection surface of a focusing element 240. In one or more embodiments, types of devices to be employed for the focusing element 240 include, but are not limited to, a single lens, a double lens, an array of lenses, a Fresnel lens, refractive elements, reflective elements (e.g., concave mirrors), and other related lens systems up to the complexity of a fully engineered telescope. The focusing element 240 is used to focus the sequence of photons 235 into the input of an optional intensity control device 242, which selects a range of operation for the system 200. Then, the sequence of photons 235 is propagated from the output of the intensity control device 242, and is propagated onto a frequency selective electromagnetic detector 160.

Once the frequency selective electromagnetic detector 160 senses the sequence of photons 235, the frequency selective imager 160 emits electrical pulses 255, 256, 257 that each have a voltage that is proportional to the respective sensed photon's energy level. The electrical pulses 255, 256, 257 are sent to the input of a processor 260 for processing and de-multiplexing. The processor 260 uses the emitted electrical pulse information to determine each of the photon's associated frequency and/or wavelength. After the electrical pulses 255, 256, 257 are de-multiplexed, the processor 260 sends the outputs 265, 266, 267 to circuits 270, 275, 280 to be summed.

For the disclosed system 200, a procedure is necessary to provide for frequency calibration. Typically, this involves using emission spectra from samples (e.g., neon and mercury) that have frequency outputs that are well characterized and traceable to a standard calibration, such as the National Institute of Standards and Technology (NIST) standards. With these outputs propagated through the frequency selective electromagnetic detector 160 and operationally correlated to the known standards, the overall system 200 will be frequency calibrated.

In addition, a procedure is necessary to provide for temporal calibration for the system 200. Generally, this involves using timing pulses at one or more frequencies that have pulse spacing that is well defined. Usually, high precision devices will be tied to absolute standards generated by NIST or some other carefully calibrated sources. With these outputs propagated though the frequency selective electromagnetic detector 160 and operationally correlated to the known standards, the overall system 200 will be temporally calibrated.

Figure 3:
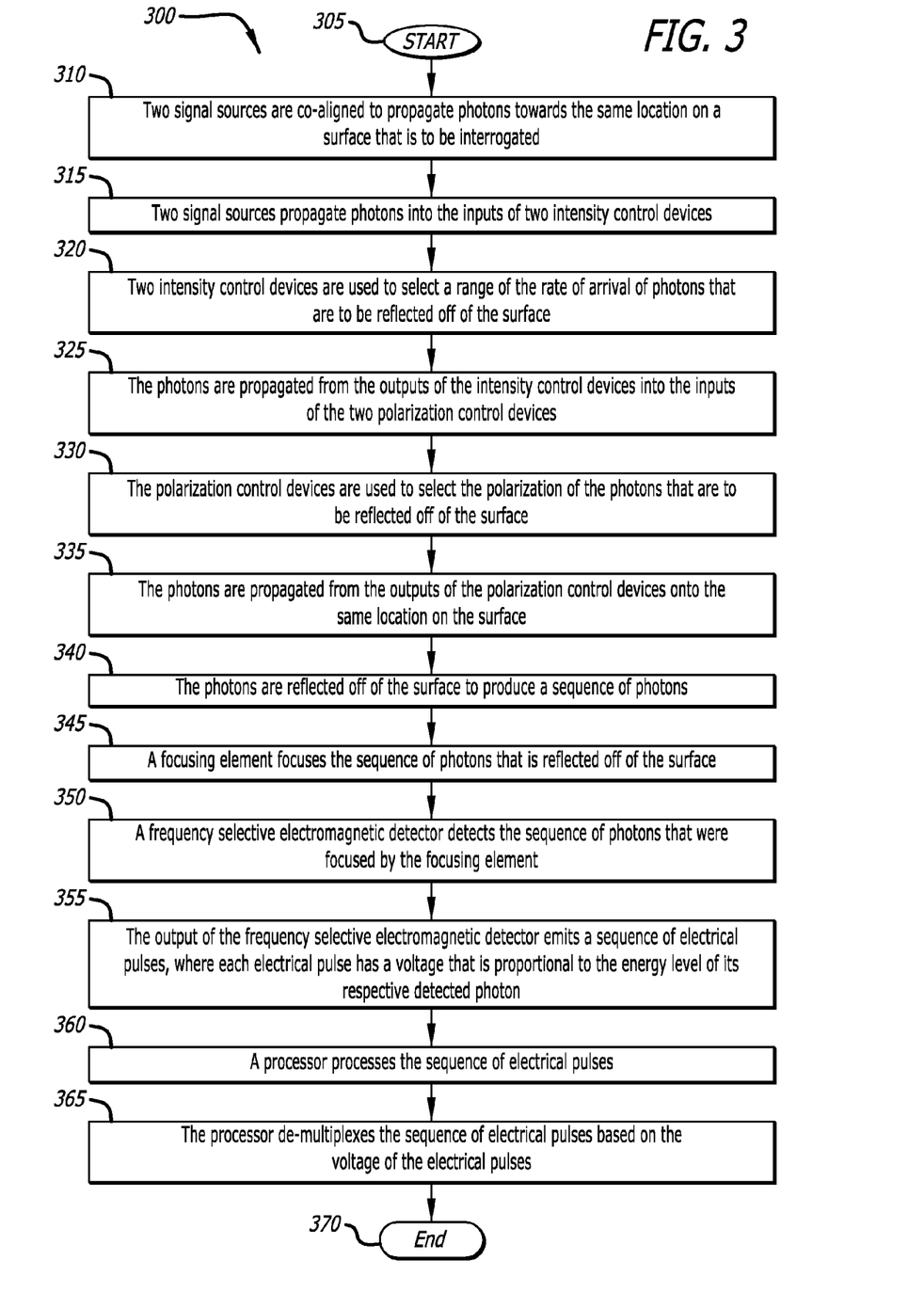
FIG. 3 displays a flow chart of the disclosed method for nonlinear optical surface sensing with a single thermo-electric detector, which employs the frequency selective electromagnetic detector of FIG. 1, in accordance with at least one embodiment of the present disclosure.

FIG. 3 displays a flow chart 300 of the disclosed method for nonlinear optical surface sensing with a single thermo-electric detector, which employs the frequency selective electromagnetic detector 160 of FIG. 1, in accordance with at least one embodiment of the present disclosure. It should be noted that, in one or more embodiments of the present disclosure, the steps as shown in the flow chart 300 may be performed in a variety of different orders than as depicted in the figure. In addition, it should be noted that in some embodiments, at least one of the steps as shown in the flow chart 300 may be omitted from the method.

At the start 305 of the disclosed method, two signal sources are co-aligned to propagate photons towards the same location on a surface that is to be interrogated 310. The two signal sources propagate photons into the input of two intensity control devices 315. The two intensity control devices are used to select a range of the rate of arrival of the photons that are to be reflected off of the surface 320. Then, the photons are propagated from the outputs of the intensity control devices into the inputs of the two polarization control devices 325. The polarization control devices are used to select the polarization of the photons that are to be reflected off of the surface 330.

The photons are then propagated from the outputs of the polarization control devices onto the same location on the surface 335. Once the photons reach the same location on the surface, the photons are reflected off of the surface to produce a sequence of photons 340. The sequence of photons is propagated through a focusing element, which focuses the sequence of photons that is reflected off of the surface 345.

Then, a frequency selective electromagnetic detector detects the sequence of photons that were focused by the focusing element 350. The output of the frequency selective electromagnetic detector emits a sequence of electrical pulses. Each of the electrical pulses has a voltage that is proportional to the energy level of its respective detected photon 355. Then, a processor processes the sequence of electrical pulses 360. The processor also de-multiplexes the sequence of electrical pulses based on the voltage of the electrical pulses 365. After the processor de-multiplexes the sequence of electrical pulses, the method ends 370.

FIG. 4 shows exemplary system responses for a linear system 420, a non-linear system 440, and a non-linear system 440 employing the disclosed frequency selective electromagnetic detector 160 of FIG. 1, in accordance with at least one embodiment of the present disclosure. In particular, FIG. 4 illustrates examples of linear 420 and non-linear system responses 440 as well as shows the advantages of the frequency selective electromagnetic detector in extracting signal frequency information. The graphs 410, 430, 450, 470 show voltages (on the vertical axes) that occur at different frequencies (on the horizontal axes).

Figure 4A:
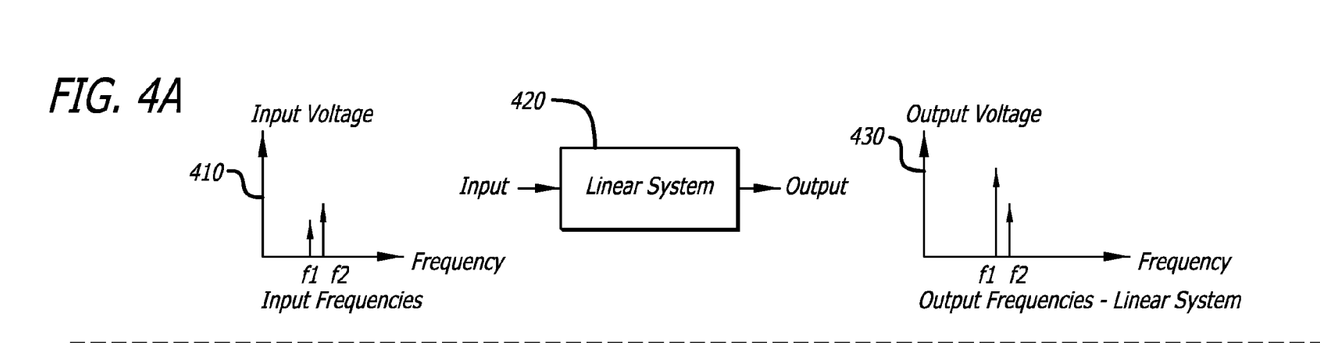
FIG. 4 shows exemplary system responses for a linear system, a non-linear system, and a non-linear system employing the disclosed frequency selective electromagnetic detector of FIG. 1, in accordance with at least one embodiment of the present disclosure.

In FIG. 4A, graph 410 shows the input voltages at frequencies f1 and f2 being inputted into the linear system 420. The resultant output voltages are shown on graph 430. The output voltages of the linear system 420 are shown to occur at the same frequencies, f1 and f2, as the input voltages shown in graph 410 because the system 420 is a linear system.

Figure 4B:
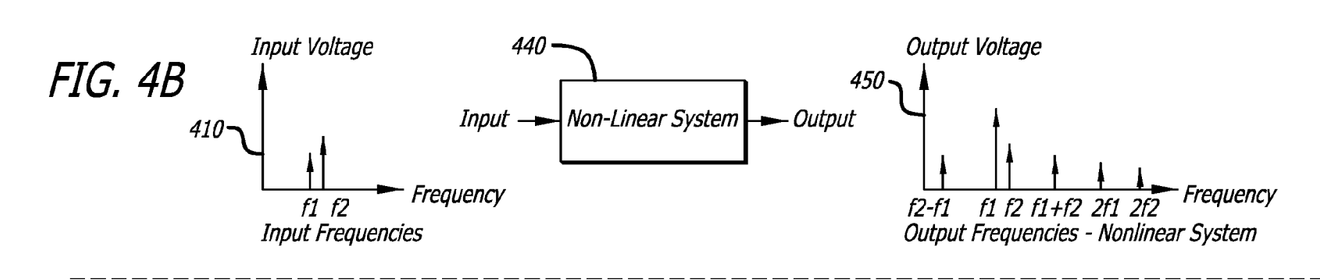

In FIG. 4B, graph 410 shows the input voltages at frequencies f1 and f2 being inputted into the non-linear system 440. The resultant output voltages are shown on graph 450. The output voltages of the non-linear system 440 are shown to occur not only at the input frequencies (f1 and f2), but also at the sum and differences of these frequencies (f1+f2 and f1−f2) as well as at the harmonics of the input frequencies (2f1, 2f2, . . . ).

Figure 4C:
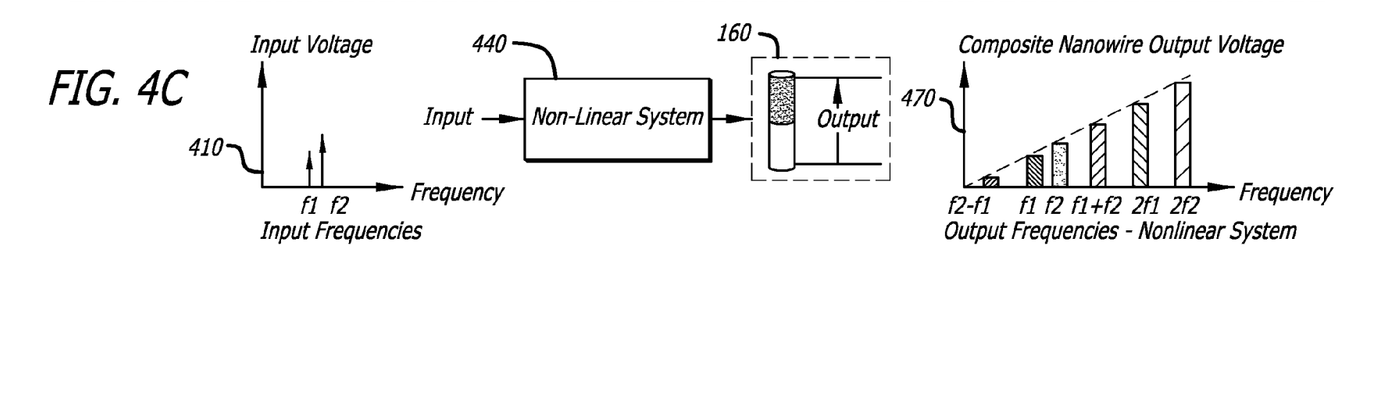

In FIG. 4C, graph 410 shows the input voltages at frequencies f1 and f2 being inputted into the non-linear system 440. The output of the non-linear system 440 is detected by the disclosed frequency selective electromagnetic detector 160, and the output of the frequency selective electromagnetic detector 160 is shown on graph 470. The frequency selective electromagnetic detector 160 voltage outputs (on the vertical axis of graph 470) are shown to be proportional to the input frequencies (on the horizontal axis of graph 470). The frequency selective electromagnetic detector output, which produces a voltage proportional to the signal input frequency, enables simple extraction of the input signal frequencies without the need for elaborate spectral filters and multiple sensors.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A system for nonlinear electromagnetic surface sensing, the system comprising:
   at least two signal sources that are co-aligned to propagate photons to a same location on a surface to be reflected off of the surface;
   at least one focusing element that focuses a sequence of photons that is reflected from the same location on the surface;
   at least one nanoparticle-sized diameter thermoelectric junction, of at least one frequency selective electromagnetic detector, that detects the sequence of photons that are focused from the at least one focusing element,
   wherein when the at least one nanoparticle-sized diameter thermoelectric junction senses at least one photon, the at least one nanoparticle-sized diameter thermoelectric junction emits at least one electrical pulse having a voltage that is proportional to an energy level related to a wavelength of the at least one photon; and
   at least one processor that processes the at least one electrical pulse and de-multiplexes a sequence of the at least one electrical pulse based on the at least one electrical pulse voltage.

2. The system for nonlinear electromagnetic surface sensing of claim 1, wherein the system is for nonlinear optical surface sensing.

3. The system for nonlinear electromagnetic surface sensing of claim 1, wherein the system further comprises at least one intensity control device that selects a range of a rate of arrival of the photons.

4. The system for nonlinear electromagnetic surface sensing of claim 3, wherein the at least one intensity control device is an electromagnetic energy filtering device.

5. The system for nonlinear electromagnetic surface sensing of claim 1, wherein the system further comprises at least one polarization control device that selects a polarization of the photons.

6. The system for nonlinear electromagnetic surface sensing of claim 5, wherein the at least one polarization control device is a polarizer.

7. The system for nonlinear electromagnetic surface sensing of claim 6, wherein the polarizer selects at least one of horizontal polarization, vertical polarization, left-hand polarization, and right-hand polarization.

8. The system for nonlinear electromagnetic surface sensing of claim 1, wherein the at least one focusing element is a signal collection lens.

9. The system for nonlinear electromagnetic surface sensing of claim 1, wherein the at least one frequency selective electromagnetic detector includes a nanowire array constructed from a plurality of nanowires of different compositions.

10. The system for nonlinear electromagnetic surface sensing of claim 9, wherein the at least one nanoparticle-sized diameter thermoelectric junction is formed between at least one of the nanowires of different compositions.

11. The system for nonlinear electromagnetic surface sensing of claim 9, wherein at least one of the nanowires in the nanowire array is manufactured from a compound material including Bismuth (Bi) and Tellurium (Te).

12. A method for nonlinear electromagnetic surface sensing, the method comprising:
    propagating, by at least two signal sources that are co-aligned, photons to a same location on a surface;
    reflecting the photons off of the surface to produce a sequence of photons;
    focusing, by at least one focusing element, the sequence of photons that is reflected from the surface;
    detecting, by at least one nanoparticle-sized diameter thermoelectric junction of at least one frequency selective electromagnetic detector, the sequence of photons that were focused by the at least one focusing element;
    emitting, from the at least one nanoparticle-sized diameter thermoelectric junction, a sequence of electrical pulses, wherein each of the electrical pulses has a voltage that is proportional to an energy level related to a wavelength of its respective detected photon;
    processing, with at least one processor, the sequence of electrical pulses; and
    de-multiplexing, with the at least one processor, the sequence of electrical pulses based on the voltage of the electrical pulses.

13. The method for nonlinear electromagnetic surface sensing of claim 12, wherein the method is for nonlinear optical surface sensing.

14. The method for nonlinear electromagnetic surface sensing of claim 12, wherein the method further comprises selecting, with at least one intensity control device, a range of a rate of arrival of the photons.

15. The method for nonlinear electromagnetic surface sensing of claim 14, wherein the at least one intensity control device is an electromagnetic energy filtering device.

16. The method for nonlinear electromagnetic surface sensing of claim 12, wherein the method further comprises selecting, with at least one polarization control device, a polarization of the photons.

17. The method for nonlinear electromagnetic surface sensing of claim 16, wherein the at least one polarization control device is a polarizer.

18. The method for nonlinear electromagnetic surface sensing of claim 17, wherein the polarizer selects at least one of horizontal polarization, vertical polarization, left-hand polarization, and right-hand polarization.

19. The method for nonlinear electromagnetic surface sensing of claim 12, wherein the at least one focusing element is a signal collection lens.

20. The method for nonlinear electromagnetic surface sensing of claim 12, wherein the at least one frequency selective electromagnetic detector includes a nanowire array constructed from a plurality of nanowires of different compositions.

21. The method for nonlinear electromagnetic surface sensing of claim 20, wherein the at least one nanoparticle-sized diameter thermoelectric junction is formed between at least one of the nanowires of different compositions.

22. The method for nonlinear electromagnetic surface sensing of claim 20, wherein at least one of the nanowires in the nanowire array is manufactured from a compound material including Bismuth (Bi) and Tellurium (Te).

* * * * *